United States Patent [19]

Foster

[11] 4,325,258
[45] Apr. 20, 1982

[54] CONICAL TRANSDUCER ULTRASONIC SCANNING

[75] Inventor: Francis S. Foster, Toronto, Canada

[73] Assignee: Ontario Cancer Institute, Toronto, Canada

[21] Appl. No.: 142,973

[22] Filed: Apr. 23, 1980

[51] Int. Cl.³ .......................................... G01N 29/04
[52] U.S. Cl. ...................................... 73/642; 310/334
[58] Field of Search ........................ 73/624, 632, 642;
367/141, 140, 151, 103, 157, 165, 155, 150;
310/334, 369, 335; 128/660

[56] References Cited

U.S. PATENT DOCUMENTS

| | | | |
|---|---|---|---|
| 2,893,239 | 7/1959 | Renaut | 73/624 |
| 3,712,119 | 1/1973 | Cross et al. | 73/624 |
| 4,103,677 | 8/1978 | Lansiart et al. | 73/621 |

FOREIGN PATENT DOCUMENTS 2711098  9/1978  Fed. Rep. of Germany ...... 128/660

OTHER PUBLICATIONS

Burckhardt, C. B., et al., "Ultrasound Axicon: A Device for Focusing over Large Depth," *J. of Acoustical Society of Amer.*, vol. 54, #6, 1973, pp. 1628–1630.
Dietz, O. R. et al., "Expanding–Aperture Annular Array," *Ultrasonic Imaging*, vol. 1, #1, 1979, pp. 56–75.

*Primary Examiner*—Anthony V. Ciarlante
*Attorney, Agent, or Firm*—Watts, Hoffmann, Fisher & Heinke Co.

[57] ABSTRACT

An ultrasonic image of improved resolution is obtained by utilizing separate transducers respectively for transmission and reception of ultrasonic pulses employed for imaging a subject, one transducer being a conical or simulated conical transducer having a line focus along the cone axis and the other transducer being aimed along the line focus of the first transducer. An area to be imaged may be scanned by moving the transducers as a unit about the subject portion to be examined.

15 Claims, 3 Drawing Figures

CONICAL TRANSDUCER ULTRASONIC SCANNING

BACKGROUND OF THE INVENTION

1. Field of the Invention

This invention relates to ultrasound imaging systems.

2. Description of the Prior Art

Ultrasound imaging systems are attractive for medical applications because they permit imaging of internal structures of the body without the use of potentially harmful forms of radiation. Numerous proposals have been made for such systems and many are in actual use. Although the systems vary widely in detail, most known systems basically utilize an ultrasonic transducer or array of transducers having coplanar emitting surface structure to beam pulses of ultrasound into a structure to be imaged and to receive reflections of those pulses. The beamed pulses are directed through the structure to be imaged in a suitable scanning pattern by mechanical and/or electronic means. One such form of scanning is known as "B-scanning".

An example of a known type of B-scanning ultrasonic system is disclosed in U.S. Pat. No. 4,014,207, issued on Mar. 29, 1977, to Meyer, et. al. for SECTOR SCANNING ULTRASONIC INSPECTION APPARATUS, which is herein expressly incorporated by reference.

A problem with such systems is lack of optimum resolution in the lateral direction, i.e., along the plane of the transducer emitting surfaces. Some improvement can be obtained utilizing large aperture transducers or transducer arrays which are electronically or acoustically focussed and/or scanned but this improvement is at the expense of a very shallow depth of field. Consequently, sophisticated means have been employed to maintain ultrasonic energy dynamically focused to a succession of points throughout a scan. The operation of such complex means, however, tends to limit the rate of scan and thus increase the time taken to generate an image. Moreover, even with such means, resolution is sometimes inadequate for reliable detection of small anomalies in the subject structure being imaged.

An example of a dynamically focused ultrasonic B-scanner is described in U.S. Pat. No. 3,090,030, issued on May 14, 1963 to Schuck for VARIABLE FOCUS TRANSDUCER. Another variant of a focused ultrasonic system is described in the following pulbication: Melen, R. D., et. al., "CCD Dynamically Focused Lenses for Ultrasonic Imaging Systems", Proceedings of the International Conference on Applications of CCD's, 1975, pp. 165-171.

SUMMARY OF THE INVENTION

I have now found that excellent lateral resolution can be maintained over a substantial depth of field by utilizing separate electroacoustic transducers for transmission and reception of ultrasound pulses utilized for imaging a structure. One transducer comprises an actual or simulated cone or conical section transducer having a line focus along its axis and extending into a subject. The other transducer is aimed axially along the line focus of the former transducer. The line of focus is moved relative to the structure being imaged to provide a desired scan of the subject portion being examined. Pulser circuitry actuates one transducer to insonify the subject along the line focus. Imaging and display circuitry and apparatus responds to electrical signals produced in response to received scattered ultrasonic energy to provide an image representation of internal subject structure.

The invention is described further with reference to the exemplary embodiment shown in the accompanying drawings, in which:

DESCRIPTION OF THE PREFERRED EMBODIMENT

Figure 1:
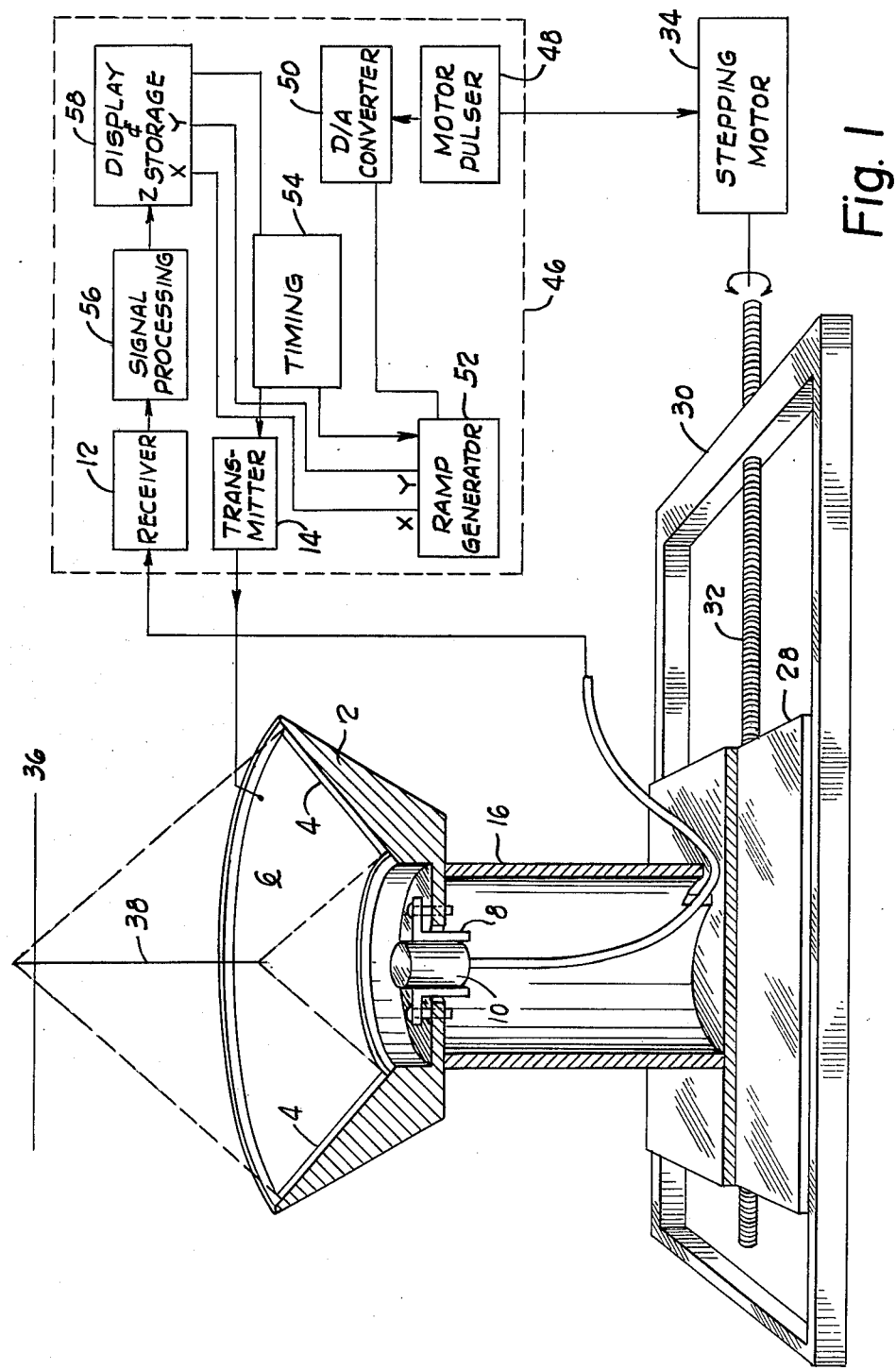
FIG. 1 is a diagramatic part sectional, part schematic drawing of one embodiment of a system incorporating the invention, intended for breast scanning.

Referring to FIG. 1, an aluminum cone 2 has bonded to its surface, by means of an epoxy resin, a sheet 4 of piezoelectric synthetic plastic, in this instance polyvinylidene fluoride sheet, thirty microns in thickness, available from Kreha Corp., of New York, NY, USA. The aluminum cone 2 acts as a back electrode while the upper surface of the plastic 4 is metallized to form a front electrode of the conical transducer. The characteristics of such a transducer are well suited to 1-10 MHz frequencies commonly employed in medical ultrasound imaging. The transducer cone 2 has an angle of 45° with respect to its axis and has an outer radius of 10 cm and an inner radius of 5 cm.

A second transducer 10, which may be a conventional disc transducer or a fixed or dynamically focused transducer, comprising, for example, an annular array, capable of operating at the desired operating frequency is mounted near the projected apex of the cone. It need not be highly directional although it must be aligned with the axis of the cone 2, which is also the focus of the transducer formed by the sheet 4. The transducer 10 is connected to a receiver 12, while the transducer formed by sheet 4 is energized by high frequency pulses gated from a pulser transmitter 14 generating an energizing potential at, typically, 3-5 MHz at 10-200 volts peak to peak.

The two transducer assembly is mounted on a column 16 which is supported by a platform 28 which can be moved laterally in a frame 30 by means of drive screw 32 which can be rotated by a stepping motor 34. Further hydraulic or screw operated means (not shown) may be provided to lift or lower the frame 30 bodily within a tank of water (not shown) in which the assembly is submerged to a depth such that the level 36 of the water is above the transducer 2. The water forms an ultrasonic coupling medium between a patient's breast to be imaged and the transducers 4 and 10. A thin plastic membrane may be provided to protect the patient from direct contact with the water and a suitable supporting couch (not shown) is of course provided to enable the patient to assume a suitable position relative to the apparatus, in accordance with known practice for ultrasonic breast imaging systems.

The present system produces an ultrasonic B-scan by operation of imaging and display circuitry as described as follows.

Figure 2A:
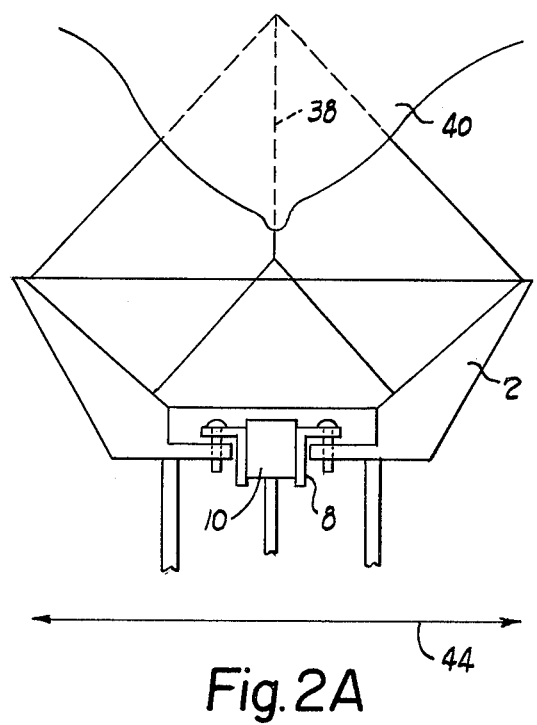
FIG. 2A illustrates use of the apparatus of FIG. 1.

In operation, the line of focus 38 intersects the breast 40 at successive locations laterally displaced across the breast in the direction indicated by the arrow 44 in FIG. 2A. The displacement is controlled by action of the motor 34, as driven by a motor pulser 38 and is in a common plane. The motor pulser 38 also applies pulses to a digital/analog converter 50 whose output is applied to a time base unit 52 comprising X and Y ramp generators. The time base unit also receives an input from a timing unit 54 which applies gating pulses to actuate the pulser transmitter 14.

Figure 2B:
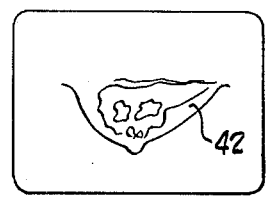
FIG. 2B is an illustration of an exemplary type of image plot obtained by use of the present invention.

The output from the D/A converter 50 is processed by the time base unit 52 to provide an X signal proportional to the lateral displacement of the platform 28. The input from the timing unit is utilized to generate a sawtooth waveform generating a Y-scan at the repetition rate of the pulses applied to the transmitter, but subject to a delay such that the scan coincides with the reception by receiver 12 of signals from the transducer 4, scattered by a breast being imaged, which are picked up by the transducer 10. The signals from the receiver 12 are processed in a signal processing unit 56, in which they may be subjected to known noise reduction and signal enhancement techniques. The processed signals are applied to a display and storage system, for example comprising a storage oscilloscope, in which the beam is Z-modulated by the received signal and deflected on the X and Y axes to provide an image of the type shown in FIG. 2B.

Electronic conversion, pulsing, timing, and processing components, comprising imaging circuitry of the described system incorporating this invention, are suitably embodied by analogous components in an ultrasonic scanner system Model 80L/DI, manufactured by Picker Corporation of Northford, Conn., U.S.A. The same applies to the scope display system.

In operation, the timing unit 54 gates short pulses of high frequency electrical energy from the transmitter 14 to the transducer 4 in which each pulse is converted into a conical wavefront of ultrasound which converges to a sharp focus on the line 38. Scattering of the ultrasound pulse takes place in the breast being imaged, the degree of scattering being dependent on the nature of the tissue causing the scattering. Most of this scattering will occur along the line of focus. Components of scattered energy from the line of focus will be picked up by the transducer 10 after a time delay dependent on the distance traveled to the transducer 10 by the scattered sound energy. Since ultrasound intensity on the line 38 will be very high compared with that elsewhere within the pick-up range of the transducer 10, the signals produced by that transducer will represent, almost solely, successive soundings along the line of focus as it is scanned through a plane intersecting the tissue being examined. It is found that the resolution and depth of field obtained are many times better than with conventional techniques when operating at similar frequencies and imaging rates. Typical conditions of operation utilize an ultrasound pulse length of 1 microsecond at a frequency of 3 MHz and a pulse repetition rate of 1 kHz.

It will be understood that the above embodiments of the invention are described by way of example only. Many variations are possible.

The functions of the conical transmitting transducer, and of the receiving transducer aligned with the line of focus of the conical transducer, may be transposed, so that the latter becomes the transmitting transducer and the former the receiving transducer. The mode chosen is largely a matter of convenience in design and electrical matching.

The conical and axial transducers themselves are subject to a wide range of constructional variation. Focussing of the output of a plane transducer could also be achieved by use of an acoustic lens to simulate a conical transducer.

The piezoelectric plastic film utilized in the exemplary embodiments of the invention has particularly convenient characteristics for this application, but there is of course no reason why other ultrasonic transducer materials, capable of being incorporated into a functional actual or simulated conical transducer, should not be used.

It will also be understood that an important aspect of the invention resides in the arrangement of transducers utilized, and that a wide range of possibilities exists as to the means utilized to scan the line focus of the conical transducer through the structure to be imaged, and to construct an image from the signals received. The angle of the cone need not be fixed at 45°. Indeed other angles would provide different information about scattering in the tissue being imaged.

What is claimed is:

1. An ultrasonic imaging device, comprising transducer means for transmitting ultrasound pulses into a portion of a structure to be imaged and receiving ultrasound scattered by said structure portion and generating signals in response thereto, means to energize said transducer means to transmit said pulses, scanning means for progressively relating said transducer means to successive portions of said structure according to a scanning pattern, and receiver and signal processing means for assembling an image from said generated signals, wherein the transducer means comprises separate transmitting and receiving transducers, one of said transducers being one of a real or simulated conical transducer having a line focus, and the other of said transducers having its axis in parallel alignment with said line focus, the scanning means being operative to move said line focus in relation to a structure to be imaged in accordance with said scanning pattern.

2. An imaging device according to claim 1, wherein the conical transducer is the transmitting transducer.

3. An imaging device according to claim 1, wherein the conical transducer is mounted on a conical support, and the other transducer is supported from near the projected cone apex in alignment with the axis of the conical transducer to form the transducer assembly.

4. An imaging device according to claim 3, wherein the conical transducer is formed by a sheet of piezoelectric synthetic plastic film.

5. An imaging device according to claim 3, wherein the scanning means includes apparatus for bodily translating the transducer assembly to move the line focus of the conical transducer in a plane intersecting a structure to be imaged.

6. An ultrasonic system for imaging internal structure of a subject, said system comprising:
 (a) a first ultrasonic transducer having an emitting face configured as at least a section of a cone having a line focus aligned with the axis of the cone;
 (b) a second transducer axially aligned with the line focus;
 (c) pulser circuitry for actuating one transducer to transmit ultrasonic energy concentrated in the region of the line focus and into the subject;
 (d) imaging circuitry coupled to the other transducer for processing electrical signals generated by the other transducer in response to ultrasonic energy from said one transducer which is scattered by a subject in the neighborhood of the line focus, and (e) a display system responsive to the processed electrical signals to produce an image describing internal subject structure.

7. The system of claim 6, wherein:
said first transducer comprises said one transmitting transducer.

8. The system of claim 6, wherein:
said second transducer comprises said one transmitting transducer.

9. The system of claim 6, further comprising:
said second transducer being configured substantially as a disc.

10. The system of claim 6, further comprising:
said second transducer being mounted near the apex of the cone defined by the first transducer.

11. The system of claim 9, further comprising:
said second transducer being mounted near the apex of the cone defined by the first transducer.

12. The system of claim 6, further comprising:
apparatus for moving the transducers as a unit in a plane.

13. An ultrasonic imaging method comprising the steps of:
(a) directing ultrasonic energy into a subject to a substantially linear focus by use of an ultrasonic transducer having an emitting face generally configured as at least a portion of a conical figure of revolution generated about said linear focus;
(b) receiving and producing electrical signals from ultrasonic energy scattered in the subject by use of a second transducer having a receiving face defining a receiving axis for receiving ultrasonic energy longitudinally propagated along said axis, said axis being aligned in parallel with said linear focus;
(c) processing electrical signals produced by the second transducer, and
(d) utilizing the processed electrical signals to produce an image describing internal subject structure.

14. An ultrasonic imaging method comprising the steps of:
(a) directing ultrasonic energy into a subject longitudinally along a transmission axis defining a line;
(b) receiving and producing electrical signals from ultrasonic energy scattered in the subject by use of a second transducer having a receiving face configured as at least a portion of a conical figure of revolution generated about said line;
(c) processing electrical signals produced by the second transducer, and
(d) utilizing the processed electrical signals to produce an image describing internal subject structure.

15. An ultrasonic transducer assembly comprising:
(a) a first transducer comprising piezoelectric material configured generally as at least a portion of a conical figure of revolution generated about a line, and
(b) a second transducer spaced from said first transducer transversely to said line and defining an axis substantially coincident with said line.

* * * * *